(12) United States Patent
Meskens

(10) Patent No.: US 8,538,545 B2
(45) Date of Patent: Sep. 17, 2013

(54) MULTI-COIL WIRELESS COMMUNICATION SYSTEM FOR AN IMPLANTABLE DEVICE

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 48 days.

(21) Appl. No.: 12/994,770

(22) PCT Filed: May 26, 2009

(86) PCT No.: PCT/AU2009/000648
§ 371 (c)(1),
(2), (4) Date: Feb. 22, 2011

(87) PCT Pub. No.: WO2009/143560
PCT Pub. Date: Dec. 3, 2009

(65) Prior Publication Data
US 2011/0137376 A1  Jun. 9, 2011

(30) Foreign Application Priority Data
May 26, 2008  (AU) ................................ 2008902596

(51) Int. Cl.
*A61N 1/00*  (2006.01)
(52) U.S. Cl.
USPC ........................................................ 607/60

(58) Field of Classification Search
USPC .................................... 607/60; 600/301, 587
See application file for complete search history.

(56) References Cited

U.S. PATENT DOCUMENTS

| 3,218,638 A | | 11/1965 | Honig |
| 5,991,664 A | * | 11/1999 | Seligman ........................ 607/60 |
| 6,009,350 A | | 12/1999 | Renken |

FOREIGN PATENT DOCUMENTS

DE  10 2004 050 616  3/2006

OTHER PUBLICATIONS

International Search Report, for PCT/AU2009/000648, mailed Jul. 31, 2009, 4 pages.

* cited by examiner

*Primary Examiner* — George Manuel
*Assistant Examiner* — Robert N Wieland
(74) *Attorney, Agent, or Firm* — Kilpatrick, Townsend & Stockton, LLP

(57) ABSTRACT

An implantable medical device comprising first and second coils each comprising one or more circular windings defining a diameter. Each of the first and second coils have a length, wherein the diameter of the one or more windings of the first coil are greater than the length of the first coil, and wherein the diameter of the one or more windings of the second coil are smaller than the length of the second coil, and wherein at least one of the one or more windings of the first coil is substantially orthogonal to at least one of the windings of the second coil.

22 Claims, 5 Drawing Sheets

MULTI-COIL WIRELESS COMMUNICATION SYSTEM FOR AN IMPLANTABLE DEVICE

CROSS-REFERENCE TO RELATED APPLICATIONS

This application is a National Stage Application of International Patent Application No. PCT/AU2009/000648, filed May 26, 2009, which claims the benefit of Australian Provisional Patent Application No. 2008902596, filed on 26 May 2008, the contents of which is hereby incorporated by reference herein.

BACKGROUND

1. Field of the Invention

The present invention is generally directed to an implantable medical device using transcutaneous radio frequency magnetic induction links between external and implantable components, and more particularly to a multi-coil wireless communication system for an implantable medical device.

2. Related Art

Auditory prostheses, such as cochlear implants, have typically comprised an external component, such as a speech processor unit, and an implantable component, such as a receiver/stimulator unit. The external component can comprise a casing, a microphone, a speech processor that converts detected sounds into coded signals and a power source. The implantable component receives the coded signals and power from the external component and outputs a stimulation signal to an electrode assembly which applies electrical stimulation to the auditory system of the implantee producing a hearing sensation corresponding to the original detected sound.

Communication between the external component and the implantable component can be provided by a radio frequency (RF) magnetic induction link comprising an external antenna and an internal implanted antenna. This (RF) link provides transcutaneous transmission of the coded signals to, and also typically from, the implantable component and can also serve to provide power to the implantable component. Such a prosthesis can utilize more than one type of external component or work together with other external or implantable components.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

In accordance with one aspect of the present invention, an implantable component of a medical device is provided. The implantable component comprises a first coil including one or more windings each defining a generally circular area having a diameter, wherein when the windings are positioned substantially parallel to one another the first coil has a length along an axis through the center of the circular areas, and wherein the diameter of the circular area defined by the windings is greater than the length of the first coil; and a second coil including a plurality of windings each defining generally circular area having a diameter, wherein when the windings are positioned substantially parallel to one another the second coil has a length along an axis through the center of the circular areas, and wherein the diameters of the circular area defined by each of the plurality of windings is smaller than the length of the second coil, wherein at least one of the one or more windings of the first coil is substantially orthogonal to at least one of the windings of the second coil.

In accordance with another aspect of the present invention, an implantable medical device is provided. The first and second coils each comprising one or more circular windings defining a diameter, wherein each of the first and second coils have a length, wherein the diameter of the one or more windings of the first coil are greater than the length of the first coil, and wherein the diameter of the one or more windings of the second coil are smaller than the length of the second coil, and wherein at least one of the one or more windings of the first coil is substantially orthogonal to at least one of the windings of the second coil.

In accordance with another aspect of the present invention, a wireless communication method for an implantable medical device comprising first and second coils each comprising one or more circular windings defining a diameter, and each coil having a length, wherein the diameter of the one or more windings of the first coil are greater than the length of the first coil, and wherein the diameter of the one or more windings of the second coil are smaller than the length of the second coil, and wherein at least one of the one or more windings of the first coil is substantially orthogonal to at least one of the windings of the second coil is provided. The method comprises: communicating wirelessly with one of a plurality of external components at a first frequency via the first coil; and communicating wirelessly with one of the plurality of external components at a second frequency via the second coil.

BRIEF DESCRIPTION OF THE DRAWINGS

By way of example only, embodiments are now described with reference to the accompanying drawings.

DETAILED DESCRIPTION

Medical prostheses, including implantable medical devices such as auditory prostheses like cochlear implants, typically rely on the use of an inductively coupled antenna coil system that acts as a radio frequency (RF) transcutaneous magnetic induction link between an external component and an implantable component. This wireless link provides a mechanism for providing power to the implantable component and also allows transfer of data from the external component to the implantable component and often, vice versa. Bilateral RF links between two or more external components and/or one or more implantable components are also utilized.

Certain aspects of the present invention are generally implantable medical device comprising first and second implantable coils. Each of the coils comprise one or more circular windings each defining a diameter, and each of the first and second coils have a length. The diameter of the one or more windings of the first coil are greater than the length of the first coil, and the diameter of the one or more windings of the second coil are smaller than the length of the second coil. Additionally, at least one of the one or more windings of the first coil is substantially orthogonal to at least one of the windings of the second coil.

Figure 1A:
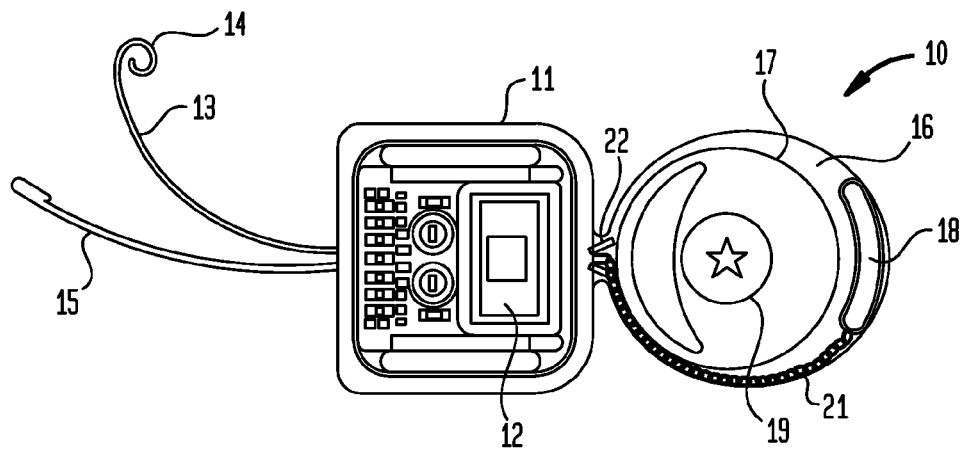
FIGS. 1A and 1B are plan and elevational views of a first embodiment of an implantable component of a cochlear implant.
Figure 1B:
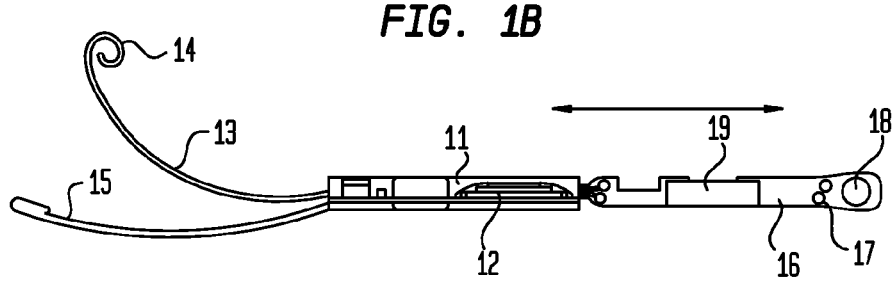

FIGS. 1A and 1B depict one embodiment of an implantable component generally as 10. The component 10 has a first hermetically sealed housing 11 that can be made of titanium or other suitable biocompatible material. It can contain a receiver and stimulator unit 12. A lead 13 extends via a feed through from a side of the housing 11 and will be seen to end in an elongate electrode carrier member 14 that is insertable within the cochlea of the implantee. The carrier member 14 can be formed of an elastomeric material, for example a silicone rubber material. The carrier member can have a plurality of electrodes mounted thereon. The electrodes can be provided in a longitudinal array. Each of the electrodes can have at least one wire, for example two, extending from each electrode back through the carrier member 14 and the lead 13 to the housing 11. The carrier 14 can have 22 electrodes, 30 electrodes, less than 20 electrodes, between 20 and 30 electrodes, or more than 30 electrodes. The electrodes can be formed of a biocompatible electrically conducting material, such as platinum. A further reference electrode 15 is also depicted. This reference electrode 15 can be mounted within or outside the cochlea of the implantee.

The implantable component 10 can be positioned subcutaneously and, for example, within a recess in the temporal bone of the implantee.

Extending from another side of the housing 11 is an elastomeric member 16. The depicted elastomeric member 16 is formed from a silicone rubber, however, other suitable elastomeric materials can be utilized. The elastomeric member contains and protects a first coil 17, acting as an antenna coil, and a further, second coil 18, acting as an antenna coil. The first antenna coil 17 is a component of the implantable part of a first transcutaneous magnetic induction link that can exist between the implantable component 10 and an external speech processor unit. The second antenna coil 18 is a component of the implantable part of a further, second transcutaneous magnetic induction link that can exist with the speech processor unit and/or another external component usable in conjunction with the prosthesis. The elastomeric member 16 also contains a substantially centrally located magnet 19 that allows a recipient to readily mount an external antenna coil in a proper orientation and position relative to the implanted component 10.

In the embodiment depicted in FIGS. 1A and 1B, the windings of the first antenna coil 17 are oriented relative to each of the coils of the second antenna coil 18 to minimize mutual inductance between the coils 17, 18.

While the embodiment depicted in FIGS. 1A and 1B only depicts one further or second antenna coil 18, it will be appreciated that more than one further antenna coil 18 could be utilized.

The first antenna coil 17 comprises a planar coil with the windings (in this embodiment there are two windings) being substantially or wholly in one plane. While the windings can be circular, other geometries can be envisaged for the first antenna coil, including square and rectangular.

The first antenna coil 17 can be disposed relative to the second antenna coil 18 so that at least one winding of the first antenna coil 17 is disposed substantially orthogonally or exactly orthogonally to at least one winding of the second antenna coil 18. In one embodiment, the second antenna coil can have a number of configurations while still having one, some or all of its windings substantially or exactly orthogonal to that of the first coil 17.

For example, the second antenna coil 18 can comprise a long coil. The long coil can have a length greater than its radius. The long coil can have one or more square windings, one or more a circular windings, one or more rectangular windings, and/or one or more elliptical windings. The long coil can have a linear axis or be bent along its length. The long coil can be an air coil or be a ferrite coil. The long coil can be encapsulated in a suitable elastomeric material.

In this and the other depicted embodiments, the respective coils 17, 18 can be formed of wires having a square cross-section, a circular cross-section, and/or some other shape. The wires can be formed from biocompatible or bio-inert materials. For example, the respective coils 17, 18 can be formed from platinum, gold, and/or suitable alloys. The respective antenna coils 17, 18 can be formed of the same material or different materials. Coatings can be used, and if present, can be biocompatible. One example of a suitable coating is parylene.

Figure 10:
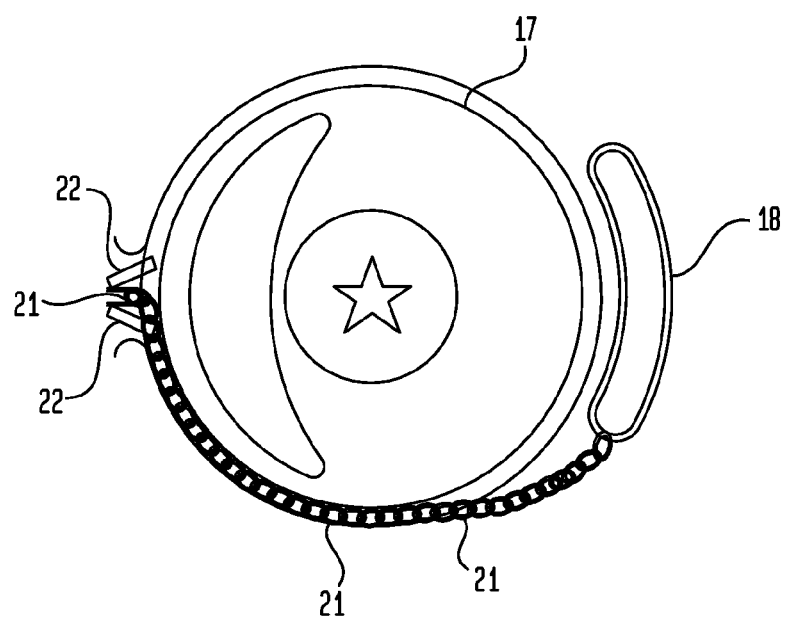
FIG. 10 is a simplified plan view of the respective antenna coils of one embodiment of an implantable component depicting twisted leads extending to the further antenna coil.

As depicted in FIG. 1A and also again in FIG. 10, leads 21 extend from the housing 11 of the implantable component 10 to the antenna coil 18. The leads 21 comprise twisted wires and are preferably relatively short to avoid parasitic inductance. Leads 22 also extend from the housing 1 to the first antenna coil 17. In the depicted embodiment, the leads 21, 22 are made of the same material as the antenna coils 17, 18 to which they extend. The leads 21, 22 also are depicted using a common inlet of a feed through into the housing 11.

It will be appreciated that in the embodiment depicted in FIGS. 1A and 1B and the other embodiments that at least one winding of the first antenna coil 17 can be disposed substantially orthogonally or exactly orthogonally to at least one winding of the second antenna coil 18. Still further, a majority or all of the windings of first antenna coil 17 can be substantially orthogonal or exactly orthogonal to the at least one winding of the second antenna coil 18. In a further embodiment, notional planes extending from the respective centers of the first antenna coil 17 and the further antenna coil 18 can be disposed substantially or exactly orthogonal to each other.

Figure 2A:
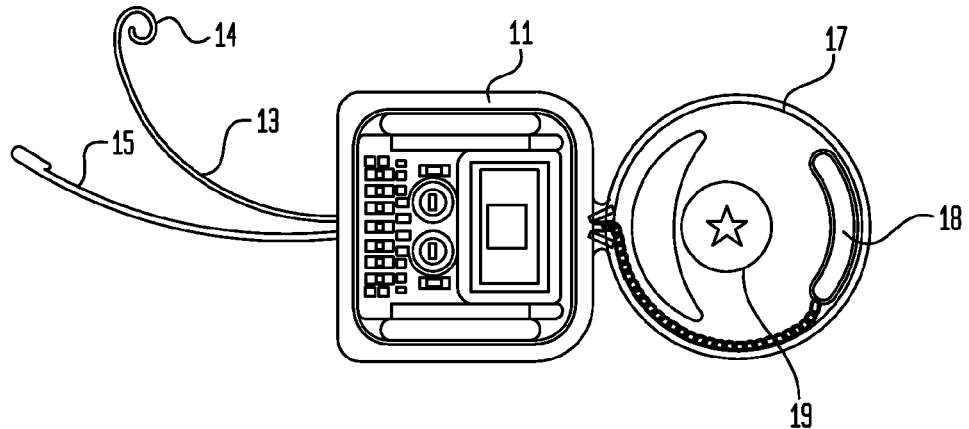
FIGS. 2A and 2B are plan and elevational views of a second embodiment of an implantable component of a cochlear implant system.
Figure 2B:
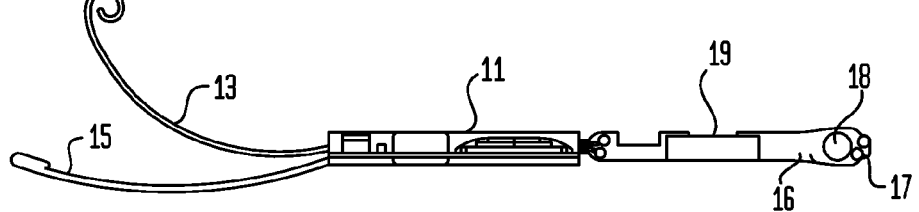
Figure 3A:
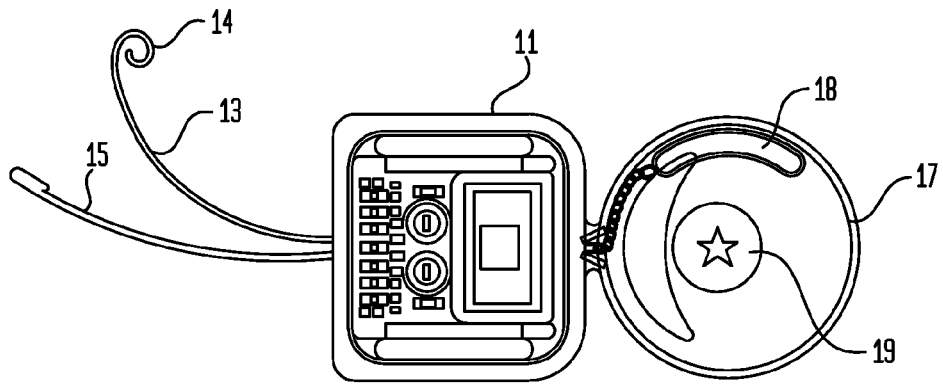
FIGS. 3A and 3B are plan and elevational views of a third embodiment of an implantable component of a cochlear implant system.
Figure 3B:
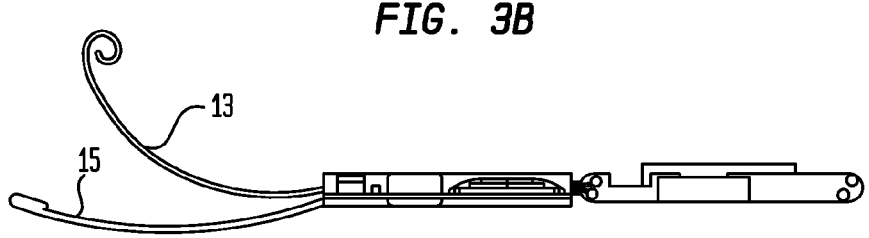
Figure 4A:
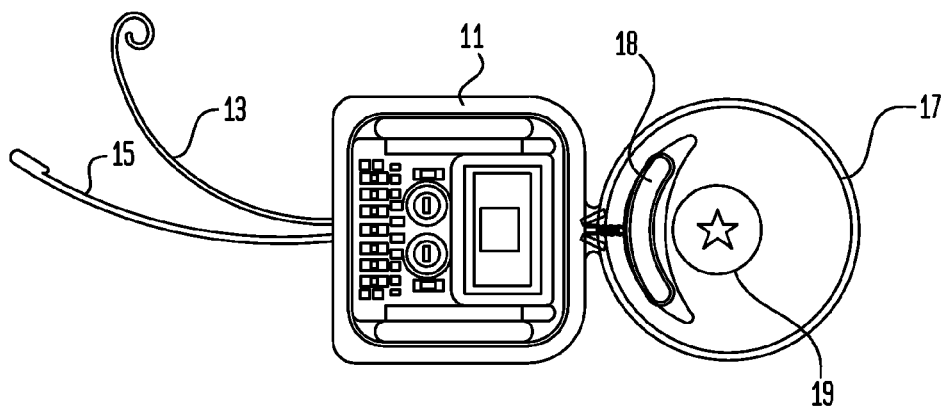
FIGS. 4A and 4B are plan and elevational views of a fourth embodiment of an implantable component of a cochlear implant system.
Figure 4B:
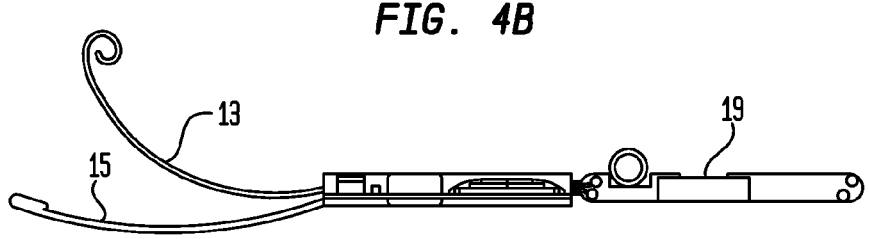

In the embodiment depicted in FIGS. 1A and 1B, the further antenna coil 18 is positioned adjacent and outside the circumference of the first antenna coil 17. In the embodiment depicted in FIGS. 2A and 2B, the further antenna coil 18 is disposed inside the area defined by the first antenna coil 17. Other but less ideal locations for the further antenna coil 18 are depicted in FIGS. 3A, 3B, 4A and 4B. In each of these embodiments, the further antenna coil 18 is located in the same plane as the first antenna coil 17.

Figure 5:
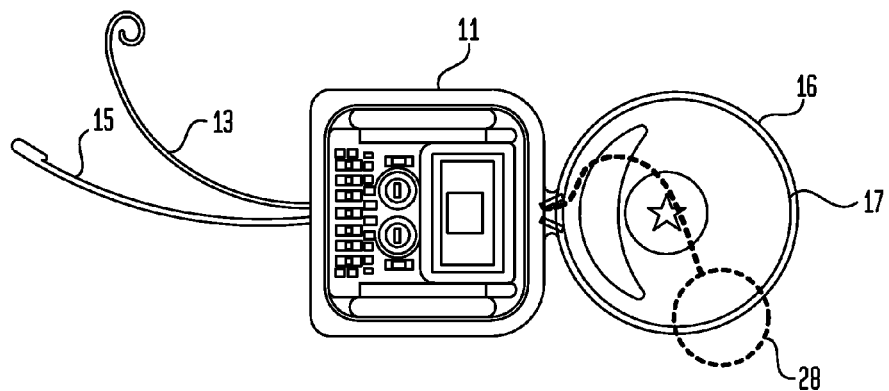
FIG. 5 is a plan view of a fifth embodiment of an implantable component of a cochlear implant system.

FIG. 5 depicts an arrangement that is less ideal than that depicted, for example, in FIGS. 1A and 1B in which the second antenna coil 28 is in a parallel plane to the first antenna coil 17 and where the ingoing and outgoing flux between the coils 17, 28 is cancelled. It is, however, anticipated that the location depicted in FIG. 5 is less preferred as the location and orientation of the second coil 28 relative to the first coil 17 will be effected by factors such as bending of the implanted coils during or following implantation and tolerances that necessarily exist in the accuracy of the manufacture and placement of the respective coils 17, 28.

Figure 6A:
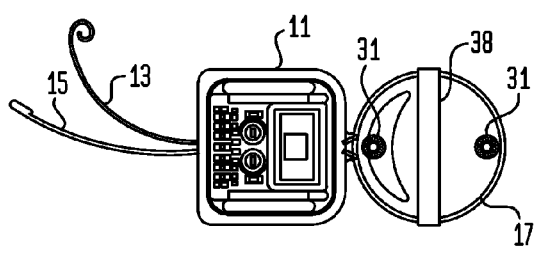
FIGS. 6A and 6B are plan and elevational views of a sixth embodiment of an implantable component of a cochlear implant system.
Figure 7A:
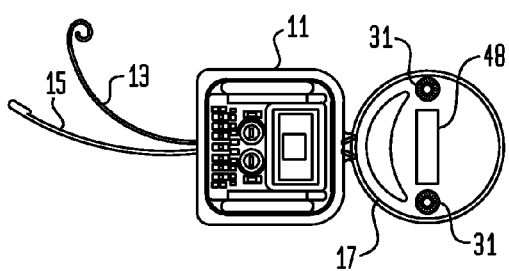
FIGS. 7A and 7B are plan and elevational views of a seventh embodiment of an implantable component of a cochlear implant system.
Figure 6B:
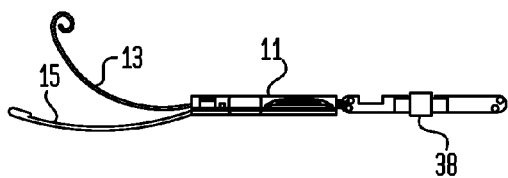
Figure 7B:
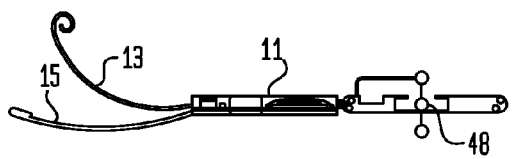
Figure 8A:
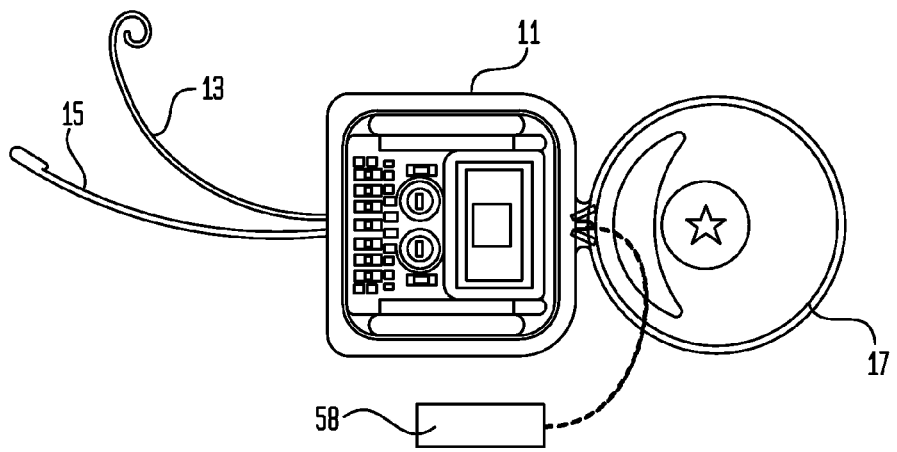
FIGS. 8A and 8B are plan and elevational views of an eighth embodiment of an implantable component of a cochlear implant system.
Figure 8B:
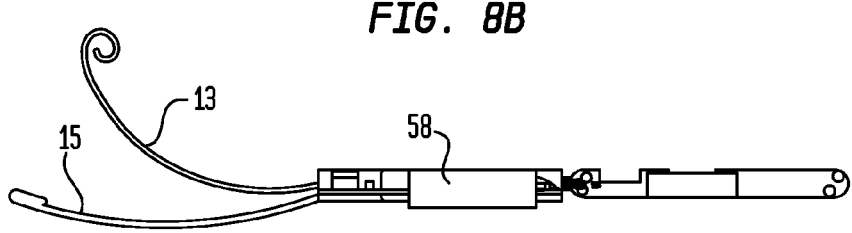
Figure 9A:
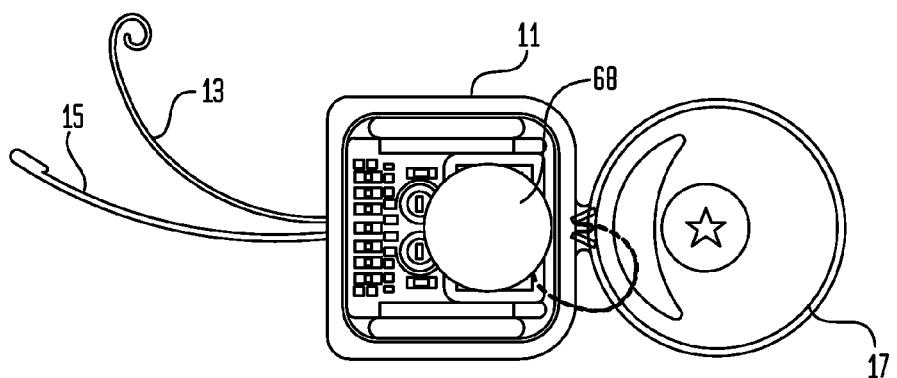
FIGS. 9A and 9B are plan and elevational views of a ninth embodiment of an implantable component of a cochlear implant system.
Figure 9B:
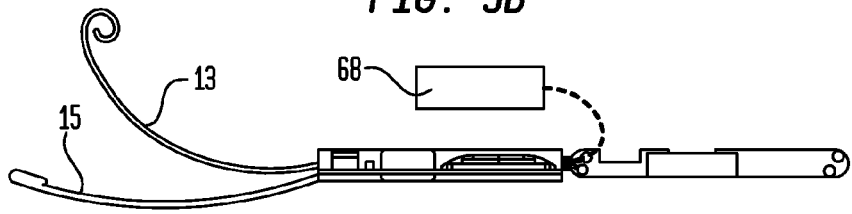

FIGS. 6 and 7 depict alternative arrangements respectively for placement of the further antenna coil 38 and 48. In these arrangements, the further antenna coils 38, 48 are placed in the center of the antenna coil 17. As this is typically the location of the magnet, in these embodiments, two magnets 31 are disposed away from the center but still within the antenna coil 17.

FIGS. 8A, 8B, 9A and 9B depict still further possible locations, respectively, for placement of a second antenna coil 58 and 68. In these embodiments, it is considered likely that at least 3 mm clearance must be provided between the coils 58, 68 and the housing 11. Again, these embodiments are considered to be less preferred than those depicted, for example, in FIGS. 1A and 1B.

Returning to FIGS. 1A and 1B, a further advantage of the depicted placement of antenna coil 18 is that the implantable component 10 has an axis of symmetry. As such, the implantable component 10 can be used on both the left and right side of the implantee.

In one embodiment, the first magnetic induction link between the first antenna 17 and an external antenna can operate at a frequency different to that of the second magnetic induction link formed by use of the further antenna coil 18. For example, the frequency of the first magnetic induction link can be at or about 2.5 MHz or 5 MHz whereas the frequency of the second magnetic induction link can be at or about 10.7 MHz.

Use of the present arrangement provides for use of a second radio frequency magnetic induction link that can be used instead or simultaneously if desired, with a first radio frequency magnetic induction link between the external component or another external component and the implantable component of a prosthesis.

The external component can comprise a speech processor unit. In one embodiment, the speech processor can comprise a behind-the-ear (BTE) unit. The unit can have a casing, suitable antennae for use in the first and/or second transcutaneous magnetic induction links, speech processor circuitry and a microphone.

According to a first aspect, the present invention is an implantable component of a prosthesis comprising a first coil that is part of a first transcutaneous magnetic induction link and comprising at least one winding; and at least one further coil that is part of a further transcutaneous magnetic induction link and comprising at least one winding; wherein said at least one winding of said first coil and said at least one winding of said at least one further coil are oriented relative to each other to minimise mutual inductance.

Use of the present arrangement provides at least one further radio frequency magnetic induction link that can be used, simultaneously if desired, with a first radio frequency magnetic induction link between the external component or another external component and the implantable component of the prosthesis.

According to a further aspect, the present invention is a prosthesis comprising an implantable component having a receiver/stimulator unit; a first coil that is part of a first transcutaneous magnetic induction link and comprising at least one winding; and at least one further coil that is part of a further transcutaneous magnetic induction link and comprising at least one winding; wherein said at least one winding of said first coil and said at least one winding of said at least one further coil are oriented relative to each to minimise mutual-inductance; and an external component.

In this aspect, the implantable component can have one, some or all of the features of the implantable component of the first aspect and as defined herein.

In either aspect, the prosthesis can comprise a hearing prosthesis. The hearing prosthesis can comprise a cochlear implant. The external component can comprise a speech processor unit. The speech processor can comprise a behind-the-ear (BTE) unit. The unit can have a casing, at least one suitable coil for use in the first and/or second transcutaneous induction links, speech processor circuitry and a microphone.

In aspects of the present invention, the first coil and/or further coil can comprise an antenna coil.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. An implantable component of a medical device comprising:
   a first coil including one or more windings each defining a generally circular area having a diameter, wherein when the windings are positioned substantially parallel to one another the first coil has a length along an axis through the center of the circular areas, and wherein the diameter of the circular area defined by the windings is greater than the length of the first coil; and
   a second coil including a plurality of windings each defining generally circular area having a diameter, wherein when the windings are positioned substantially parallel to one another the second coil has a length along an axis through the center of the circular areas, and wherein the diameters of the circular area defined by each of the plurality of windings is smaller than the length of the second coil,
   wherein at least one of the one or more windings of the first coil is substantially orthogonal to at least one of the windings of the second coil;
   wherein the second coil has a bent configuration substantially following the curvature of the first coil.

2. The implantable component of claim 1, wherein the implantable component is configured to utilize the first coil to wirelessly communicate with an external component at a first frequency, and is configured to utilize the second coil to communicate with the external component and at a second frequency.

3. The implantable component of claim 1, wherein the second coil is disposed substantially in the circular area defined by the at least one winding first coil and is positioned adjacent to the windings of the first coil.

4. An implantable component of a medical device comprising:
   a first coil including one or more windings each defining a generally circular area having a diameter, wherein when the windings are positioned substantially parallel to one another the first coil has a length along an axis through the center of the circular areas, and wherein the diameter of the circular area defined by the windings is greater than the length of the first coil; and
   a second coil including a plurality of windings each defining generally circular area having a diameter, wherein when the windings are positioned substantially parallel to one another the second coil has a length along an axis through the center of the circular areas, and wherein the diameters of the circular area defined by each of the plurality of windings is smaller than the length of the second coil, wherein at least one of the one or more windings of the first coil is substantially orthogonal to at least one of the windings of the second coil;

wherein the second coil is disposed outside of the circular area defined by the at least one winding first coil and is positioned adjacent to the windings of the first coil.

5. The implantable component of claim 4, wherein the implantable component is configured to utilize the first coil to wirelessly communicate with an external component at a first frequency, and is configured to utilize the second coil to communicate with the external component and at a second frequency.

6. An implantable component of a medical device comprising:

a first coil including one or more windings each defining a generally circular area having a diameter, wherein when the windings are positioned substantially parallel to one another the first coil has a length along an axis through the center of the circular areas, and wherein the diameter of the circular area defined by the windings is greater than the length of the first coil; and a second coil including a plurality of windings each defining generally circular area having a diameter, wherein when the windings are positioned substantially parallel to one another the second coil has a length along an axis through the center of the circular areas, and wherein the diameters of the circular area defined by each of the plurality of windings is smaller than the length of the second coil, wherein at least one of the one or more windings of the first coil is substantially orthogonal to at least one of the windings of the second coil;

wherein the implantable component further comprises:
a housing containing a receiver and stimulator unit; and
a plurality of leads connecting the second coil and the receiver and stimulator unit, wherein the leads are disposed outside the circular area defined by the windings of the first coil.

7. The implantable component of claim 6, wherein the leads are disposed adjacent to the circumference of the first coil such that the leads substantially follow the shape of the circumference of the first coil.

8. The implantable component of claim 6, wherein the implantable component is configured to utilize the first coil to wirelessly communicate with an external component at a first frequency, and is configured to utilize the second coil to communicate with the external component and at a second frequency.

9. The implantable component of claim 7, wherein the leads comprise twisted wires.

10. An implantable medical device comprising:

first and second coils each comprising one or more circular windings defining a diameter, wherein each of the first and second coils have a length;

wherein the diameter of the one or more windings of the first coil is greater than the length of the first coil;

wherein the diameter of the one or more windings of the second coil is smaller than the length of the second coil;

wherein at least one of the one or more windings of the first coil is substantially orthogonal to at least one of the windings of the second coil; and wherein the second coil has a bent configuration substantially following the curvature of the first coil.

11. The implantable component of claim 10, wherein the second coil is disposed substantially in the circular area defined by the at least one winding first coil and is positioned adjacent to the windings of the first coil.

12. The implantable medical device of claim 10, wherein the implantable medical device is configured to utilize the first coil to wirelessly communicate with an external component at a first frequency, and is configured to utilize the second coil to communicate with the external component and at a second frequency.

13. An implantable medical device comprising:

first and second coils each comprising one or more circular windings defining a diameter, wherein each of the first and second coils have a length;

wherein the diameter of the one or more windings of the first coil is greater than the length of the first coil;

wherein the diameter of the one or more windings of the second coil is smaller than the length of the second coil;

wherein at least one of the one or more windings of the first coil is substantially orthogonal to at least one of the windings of the second coil; and wherein the second coil is disposed outside of the circular area defined by the at least one winding first coil and is positioned adjacent to the windings of the first coil.

14. The implantable medical device of claim 13, wherein the implantable medical device is configured to utilize the first coil to wirelessly communicate with an external component at a first frequency, and is configured to utilize the second coil to communicate with the external component and at a second frequency.

15. An implantable medical device comprising:

first and second coils each comprising one or more circular windings defining a diameter, wherein each of the first and second coils have a length;

wherein the diameter of the one or more windings of the first coil is greater than the length of the first coil;

wherein the diameter of the one or more windings of the second coil is smaller than the length of the second coil;

wherein at least one of the one or more windings of the first coil is substantially orthogonal to at least one of the windings of the second coil; and wherein the medical device further comprises:

a housing containing a receiver and stimulator unit; and a plurality of leads connecting the second coil and the receiver and stimulator unit, wherein the leads are disposed outside the circular area defined by the windings of the first coil.

16. The implantable medical device of claim 15, wherein the leads are disposed adjacent to the circumference of the first coil such that the leads substantially follow the shape of the circumference of the first coil.

17. The implantable medical device of claim 15, wherein the implantable medical device is configured to utilize the first coil to wirelessly communicate with an external component at a first frequency, and is configured to utilize the second coil to communicate with the external component and at a second frequency.

18. The implantable medical device of claim 16, wherein the leads comprise twisted wires.

19. An implantable component of a medical device comprising:
- a first coil including one or more windings each defining a generally circular area having a diameter, wherein when the windings are positioned substantially parallel to one another the first coil has a length along an axis through the center of the circular areas, and wherein the diameter of the circular area defined by the windings is greater than the length of the first coil; and
- a second coil including a plurality of windings each defining generally circular area having a diameter, wherein when the windings are positioned substantially parallel to one another the second coil has a length along an axis through the center of the circular areas, and wherein the diameters of the circular area defined by each of the plurality of windings is smaller than the length of the second coil; and
- a magnet configured to couple with a corresponding external magnet of an external component so as to magnetically attract the external component towards the implantable component;
- wherein at least one of the one or more windings of the first coil is substantially orthogonal to at least one of the windings of the second coil.

20. The implantable component of claim 19, wherein:

the magnet is disposed substantially in the circular area of the first coil.

21. The implantable component of claim 20, wherein:

the magnet has an axis of symmetry; and the axis of symmetry of the magnet is substantially parallel to the axis through the center of the circular areas of the first coil.

22. The implantable component of claim 20, wherein:

the magnet is a first magnet;

the implantable component further includes:
- a second magnet configured to couple with a corresponding external magnet of an external component so as to magnetically attract the external component towards the implantable component;

the first and second magnets have axes of symmetry; and the axes of symmetry of the first and second magnets are disposed symmetrically with respect to the axis through the center of the circular areas of the first coil, respectively.

* * * * *